United States Patent
Coyle et al.

(10) Patent No.: US 6,383,999 B1
(45) Date of Patent: May 7, 2002

(54) PERSONAL WASHING BAR HAVING ADJACENT EMOLLIENT RICH AND EMOLLIENT POOR PHASES

(75) Inventors: Laurie Ann Coyle, Park Ridge, NJ (US); Albert Joseph Post, Orange; Syed Husain Abbas, Seymour, both of CT (US); Gail Beth Rattinger, Teaneck, NJ (US); Michael Massaro, Congers, NY (US); Harry Crookham, Lyndhurst, NJ (US)

(73) Assignee: Unilever Home & Personal Care USA. division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/734,802

(22) Filed: Dec. 12, 2000

Related U.S. Application Data

(60) Provisional application No. 60/181,515, filed on Feb. 10, 2000.

(51) Int. Cl.[7] .................................................. A61K 7/50
(52) U.S. Cl. ....................... 510/146; 510/151; 510/153; 510/155
(58) Field of Search ................................. 510/146, 151, 510/153, 155, 156, 449, 450, 148

(56) References Cited

U.S. PATENT DOCUMENTS

| | | |
|---|---|---|
| 4,017,574 A | 4/1977 | Joshi |
| 4,996,000 A | 2/1991 | Redeker |
| 5,154,849 A | 10/1992 | Visscher et al. |
| 5,783,536 A | 7/1998 | Farrell et al. |
| 5,858,939 A | 1/1999 | Tsaur |
| 5,965,501 A | 10/1999 | Rattinger et al. |
| 5,981,464 A | 11/1999 | He et al. |

FOREIGN PATENT DOCUMENTS

| | | |
|---|---|---|
| DE | 4005183 A1 | 8/1990 |
| EP | 0808895 A2 | 11/1997 |
| WO | 94/03151 | 2/1994 |
| WO | 94/03152 | 2/1994 |
| WO | 98/27193 | 6/1998 |

OTHER PUBLICATIONS

EP 01/01158 dated May 02, 2001–5 page.

*Primary Examiner*—Necholus Ogden
(74) *Attorney, Agent, or Firm*—Alan A. Bornstein

(57) ABSTRACT

The present invention relates to a multiphase cleansing bar having a plurality of phases of cleansing material. Adjacent phases preferably have different concentration levels of benefit components respectively and all the phases individually preferably have a substantially similar cleansing base consisting of a syndet base, a soap base, or mixtures thereof. These benefit components are emollients, moisturizers, nutrients, anti-aging materials etc. Segregation of the benefit rich component is expected to result in improved deposition of the benefit components on the skin during the product application, which improves the moisture barrier properties of the skin. Chemical and Theological compatibility between the phases is maximized and recycling of the product during production is facilitated with the use of a uniform cleansing base. Methods of producing the inventive bar by extruding and melt casting are also disclosed.

12 Claims, 1 Drawing Sheet

PERSONAL WASHING BAR HAVING ADJACENT EMOLLIENT RICH AND EMOLLIENT POOR PHASES

This application claims the benefit of U.S. provisional application No. 60/181,515 filed Feb. 10, 2000 abandoned.

FIELD OF THE INVENTION

The present invention relates to multiphase cleansing bar.

BACKGROUND OF THE INVENTION

It has long been a desirable goal to deliver some kind of emollient, moisturizer or nutrient benefit component (e.g., Fatty acids, triglycerides, glycerin, petrolatum, or silicone compounds etc.) to the skin through a personal wash composition for moisturization, etc.

In liquid cleansers, for example, cationic hydrophilic polymers such as Polymer JR® from Amerchol or Jaguar® from Rhone Poulenc have been used-to enhance delivery of benefit agents (WO 94/03152; and WO 94/03151). In applicants' recently issued U.S. Pat. No. 5,965,501 to Rattinger et al., separate emollient droplets act as a structure to entrap the benefit agent in concentrated form.

Delivery of benefit agents (e.g., Fatty acids, triglycerides, glycerin, silicone compounds etc.) has proven difficult in bar compositions for a number of reasons. If the benefit agent does not remain sufficiently discrete from other components in the bar composition, for example, the generally hydrophobic benefit agent will interact with the hydrophobic portion of the surfactant compounds in the bar mix rather than be free to deposit on the skin or other substrate. Thus, little or no benefit agent will be free in the final bar (after milling, plodding and extrusion of chips) to be delivered to the skin. Most of the benefit components are liquids and can interact with surfactants to form a liquid crystalline phase. Thus the use of a high level of these benefit agents can make the bar soft, which also leads to difficulty in processing.

U.S. Pat. No. 4,017,574 to Joshi, issued Apr. 12, 1977 discloses a process for making a multicolored soap bar where a coloring agent is dispersed in a meltable solid vehicle and introduced into a base soap material before extrusion to yield a striped soap bar. The meltable solid material may be wax or wax-like and comprise one or more benefit agents with the limitation that the melting point of the solid material is above 100° F. and is compatible with the water soluble dye. However, this meltable solid material may not be compatible with the soap base of the bar resulting in cracking and adhesive failure over time.

U.S. Pat. No. 5,154,849 to Visscher et al. issued Oct. 13, 1992, teaches bar compositions containing a silicone skin mildness/moisturizing aid component as small domains. In one embodiment, the silicone component may be mixed with a carrier which is selected to facilitate incorporation of the silicone in the product. The preferred carrier is said to be polyethylene glycol. At column 16, the reference describes that silicone is mixed into melted Carbowax (polyethylene glycol). The mixture is cooled to form flakes and the flakes are preferably added to an amalgamator with the rest of the formulation ingredients. The carbowax carrier material may not be compatible with the soap base of the bar resulting in rheological and chemical incompatibility.

In the subject invention, the benefit agent is distributed in the cleansing bar in adjacent benefit agent rich and poor phases. In a preferred embodiment, the phases are situated along the major axis of the cleansing bar as stripes. Each phase or layer preferably has substantially the same cleansing base such as a syndet base, a natural soap base, or a blend thereof and is both Theologically and chemically compatible. Rheological compatibility is herein defined as having similar flow properties under extrusion processing conditions. Chemical or interphase compatibility is herein defined as the absence of interfacial cracking or splitting and having similar wear rates or mush properties between abutting phases. Such interphase compatibility is believed to be due to the similarity in free energy at the surface of the abutting phases.

In prior art methods, the addition of the benefit components in amalgamator and further processing through the refiners and plodders leads to mixing of the benefit components in the bulk of the formulation. By contrast, the alternating emollient rich and poor phases of the invention do not get mixed because the two phases are coextruded near the cone at the final plodding stage.

In another embodiment of the invention, the chemically compatible emollient rich and emollient poor phases can be melt cast adjacent to each other.

Whether a result of an extrusion or a casting process, the segregation of the phases or domains can lead to higher deposition of the benefit components during the application of the inventive product. Preferably the cleansing base of the adjacent phases, used for the product, is substantially the same, and rheological and interphase compatibility will therefore be maximized.

SUMMARY OF THE INVENTION

In the subject invention, applicants have unexpectedly found that, when the cleansing base in which the highest concentration of emollients are found ("emollient rich phases or layers") is positioned adjacent to a rheologically and chemically compatible lower emollient concentration phase or layer of the cleansing bar "(emollient deficient phase or layer"), enhanced deposition of benefit agent occurs without the disadvantage of phase incompatibility problems, lather depression and recycling difficulties. The domains can be in the form of stripes, striations, alternating blocks, swirling, random distribution of the benefit domains etc. Preferably the multiphase cleansing bar will be striped as shown in FIGS. 1 and 2. In the specification, the terms emollient deficient phase or layer and emollient poor phase or layer are used interchangeably and mean the same thing as defined above.

Specifically, the invention comprises a multiphase cleansing bar comprising:

(a) a plurality of phases of cleansing material;
(b) each of said cleansing phases being Theologically compatible;
(c) said plurality of phases having at least one emollient rich phase, at least one emollient deficient phase, and at least one interface therebetween;
(d) said emollient rich phase containing an emollient composition in the amount of 0.1 to 50 weight %, said emollient deficient phase containing an emollient composition in the amount of 0 to 25 weight %; and said emollient rich phase having a higher total emollient composition concentration compared to the emollient poor phase.

Preferably the emollient rich and poor phases will have substantially the same cleansing base selected from the group consisting of a syndet base, a soap base, or a mixture thereof.

Preferably the emollient composition concentration in the emollient rich layer based on the total cleansing bar, is 0.5 to 30 weight %, more preferably 1 to 20 weight %. Preferably the emollient composition concentration in the emollient poor phase is 0 to 10 weight %, more preferably 0 to 5 weight %, base on the total cleansing bar. Preferably the emollient composition concentration in the emollient rich phase is 5 times the emollient composition concentration in the emollient poor phase. More preferably the emollient composition concentration in the emollient rich phase is 10 times the emollient composition concentration in the emollient poor phase.

In a preferred embodiment of the invention, the cleansing bar comprises:

(a) a plurality of layers or phases of cleansing material;

(b) each of said cleansing layers having a substantially uniform cleansing base selected from the group consisting of a syndet base, a soap base, or mixtures thereof;

(c) said plurality of layers having alternating emollient rich layers and emollient poor layers;

(d) said emollient rich layers uniformly containing an emollient composition in the amount of 0.1 to 50 weight %, said emollient poor layers uniformly containing an emollient composition in the amount of 0 to 5 weight %; and said emollient rich layers having at least 2 times the emollient composition concentration compared to the emollient poor layers.

The surfactant system or cleansing base may be a pure soap surfactant system having tallowate and/or vegetable oil soaps such as palmate, cocoate, palmkernelate, any other vegetable oil soap or a mixture of these at any ratio. Preferably the tallowate/cocoate blend is used in the ratio range of 90/10 to 50/50. Most preferably it is in the ratio range of 90/10 to 60/40. Preferably the vegetable oil is selected from the group consisting of palm oil, coconut oil, palm kernal oil, palm stearin, and hydrogenated rice bran oil.

The surfactant system also may comprise a synthetic detergent system ("syndet"). Preferably the syndet system comprises:

(a) a first synthetic surfactant which is an anionic surfactant; and/or (b) a second surfactant selected from -the group consisting of a second anionic surfactant different from the first, a nonionic, an amphoteric and mixtures thereof.

A particularly preferred syndet surfactant system comprises acyl isethionate as the first anionic and a sulfosuccinate or a betaine surfactant or mixtures of the two as the second surfactant. Alternatively the surfactant system may be a blend of pure soap and synthetic surfactants.

In accordance with these and other aspects of the invention, the invention will now be described with reference to the accompanying drawings where like numerals represent like features.

DETAILED DESCRIPTION OF THE INVENTION

Figure 1:
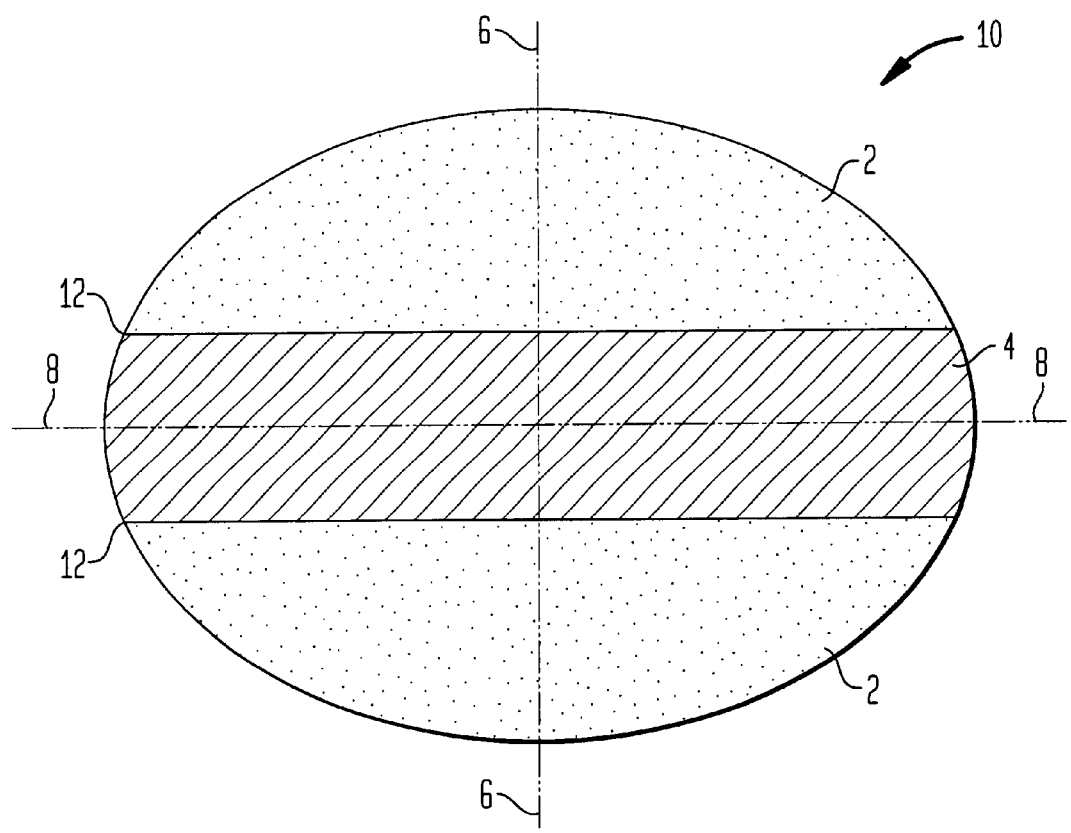
FIG. 1 is a top planar view showing one embodiment of a multiphase cleansing bar of the present invention.
Figure 2:
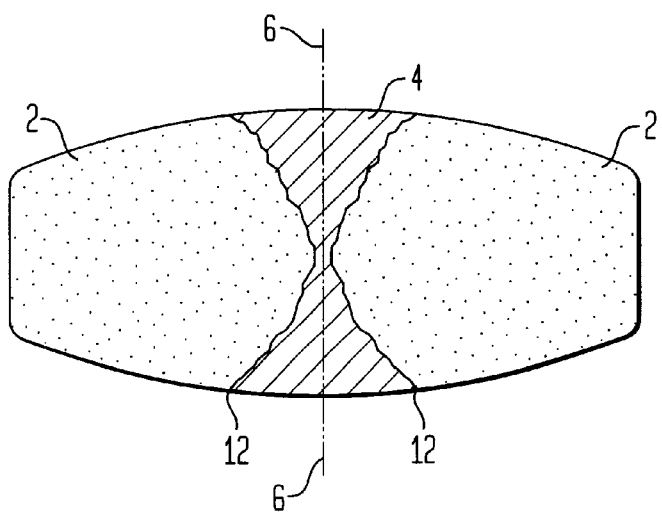
FIG. 2 is a cross section taken along line 6—6 of FIG. 1.

Referring to FIG. 1, multiphase cleansing bar 10 has alternating emollient rich layers 4, and emollient poor layers 2 separated by interface 12. Also depicted in FIG. 1 is major axis line 8—8 and minor axis line 6—6 of multi-layer soap bar 10 . FIG. 2 shows a cross section taken along line 6—6 of FIG. 1.

In this embodiment of the inventive multiphase cleansing bar, the cleansing base of the emollient rich layer 4 is substantially the same as the adjacent, emollient poor layer 2. The ratio of the width of the emollient rich layer 4 to the emollient poor layer 2 s preferably 1 to 20, more preferably 1 to 5.

Compared to the inventive cleaning bar, enhanced deposition is not seen for cleansing bars in which emollient is simply added during the mixing, milling and/or refining steps without segregating the emollient into emollient rich phases or layers. By segregating the emollient rich phase from emollient poor phase, it is believed that the emollient is less available to interact with surfactants in the bar and is therefore more available to deposit on skin or other substrate during application. This segregation also helps in keeping a hydrophobic benefit component apart from the other major functional components of the formulation. In this way, the benefit component will be less likely to negatively impact the user properties such as lather.

The emollient containing compositions may also comprise structuring aid/filler, free fatty acid and/or water.

The invention will now be described in further detail below.

COMPOSITION OF EMOLLIENT RICH PHASE

Benefit Agent

The emollient or benefit agent of the subject invention may be a single benefit agent component, or it may be a benefit agent compound added alone or via a carrier into the process stream. Further the benefit agent may be a mixture of two or more compounds, one or all of which may have a beneficial aspect. In addition, the benefit agent itself may act as a carrier for other components one may wish to add to the bar composition.

The benefit agent can be an "emollient oil" by which is meant a substance which creates a barrier on the skin (stratum comeum) and reduces the excessive water loss, maintaining the skin soft and moist.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride, 2-ethylhexanoic acid glyceride and ricinolyl monomaleate triglyceride.

(c) waxes such as carnauba, spermaceti, beeswax, lanolin and derivatives thereof;

(d) hydrophobic plant extracts;

(e) hydrocarbons such as liquid paraffins, petrolatum, microcrystalline wax, ceresin, squalene, and pristan.

(f) higher alcohols such as lauryl, cetyl, stearyl, oleyl, behenyl, cholesterol and 2-hexydecanol alcohol;

(g) esters such as cetyl octanoate, benzyl laurate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(h) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(i) lipids such as cholesterol, ceramides, sucrose esters and pseudo-ceramides as described in European Patent Specification No. 556,957;

(j) vitamins such as vitamin A and E, and vitamin alkyl esters, including those vitamin C alkyl esters;

(k) sunscreens such as octyl methoxyl cinnamate (Parsol MCX) and butyl methoxy benzoylmethane (Parsol 1789);

(l) phospholipids; and (m) silicone compounds such as dimethicones, cyclomethicones, silanols, silicone surfactants, modified silicone compounds with hydrocarbon chains. Especially preferred silicone emollients include: dimethicones having viscosity greater than about 50,000 centipoise and polydimethylsiloxane having a viscosity of about 60,000 centistokes.

(n) hydroxyacids and their salts or esters.

(o) mixtures of any of the foregoing components.

Other Components

Water comprises 0 to 20% of the inventive cleansing bar, preferably 0 to 12%.

In addition the emollient rich phase may comprise 0 to 45%, preferably 5 to 25% fatty acid, i.e., $C_8$ to $C_{24}$ fatty acid. Generally, this includes straight chain or branched chain, saturated fatty acid or unsaturated fatty acids but it is not necessarily limited to this.

The phases may further comprise a structuring aid and/or filler which can be a fatty acid as described above or ester derivative; or preferably straight and saturated $C_8$ to $C_{24}$ alcohol or ether derivatives.

CLEANSING BASE

The bars of the invention also comprise a cleansing base which comprises surfactants, structuring aid/filler, free fatty acid and water.

The surfactant system comprises about 5% to 90% by wt. of the inventive cleansing bar wherein the surfactant is selected from the group consisting of soap (pure soap surfactant systems are included), anionic surfactant, nonionic surfactant, amphoteric/zwitterionic surfactant, cationic surfactant and mixtures thereof.

Surfactant System

The term "soap" is used herein in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be ammonium, potassium, magnesium, calcium or a mixture of these soaps. The soaps useful herein are the well known alkali metal salts of aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of tallow, and vegetable oil. More preferably the vegetable oil is selected from the group. consisiting of palm oil, coconut oil, palm kernal oil, palm stearin, and hydrogenated rice bran oil, or mixtures thereof, since these are among the more readily available fats. Especially preferred is coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. As mentioned above, the soap may preferably be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^4O_2CCH_2CH(SO_3M)CO_2M;\ and$$

amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R'CON(CH_3)CH_2CO_2M,$$

wherein R ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total bar composition. Preferably, this component is present from about 30% to about 60%.

The acyl isethionate may be an alkoxylated isethionate such as is described in Hardi et al., U.S. Pat. No. 5,393,466, hereby incorporated by reference. This compound has the general formula:

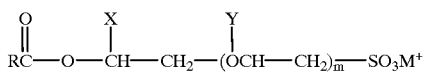

wherein R is an alkyl group having 8 to 18 carbons, m is an integer from 1 to 4, X and Y are hydrogen or an alkyl group having 1 to 4 carbons and M$^+$ is a monovalent cation such as, for example, sodium, potassium or ammonium.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

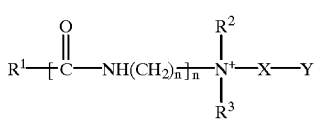

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;

m is 2 to 4;
n is 0 to 1;
X is alkylene of 1 to 3 carbon atoms optionally substituted with hydroxyl, and
Y is $-CO_2-$ or $SO_3-$ Suitable amphoteric detergents within the above general formula include simple betaines of formula:

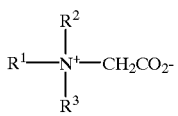

and amido betaines of formula:

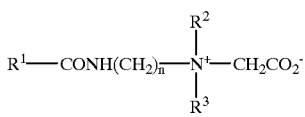

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

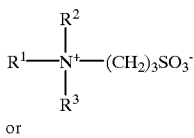

or

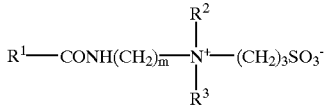

where m is 2 or 3, or variants of these in which $-(CH_2)_3 SO_3^-$ is replaced by

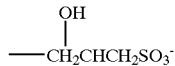

In these formulae $R^1$, $R^2$ and $R^3$ are as discussed previously.

The nonionic which may be used as the second component of the invention include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Although the bar may be a pure soap bar, preferably the surfactant system of this chip (forming the surfactant system in the bar) comprises:

(a) a first synthetic surfactant which is anionic; and/or
(b) a second surfactant selected from the group consisting of a second anionic different from the first, a nonionic, an amphoteric and mixtures thereof.

The first anionic can be any of those recited above, but is preferably a $C_8$ to $C_{18}$ isethionate as discussed above. Preferably acyl isethionate will comprise 10% to 90% by wt. total bar composition.

The second surfactant is preferably a sulfosuccinate, a betaine, any other surfactant or a mixture of two or more of these surfactants. The second surfactant or mixture of surfactant will generally comprise 1% to 20% total bar composition. A particularly preferred composition comprises enough sulfosuccinate to form 3–10% total bar compositions and enough betaine to form 1–5% of total bar composition.

The cleansing base also comprises 0 to 20% water, preferably 0 to 12% by wt. water.

The cleansing base further comprise 0.1 to 80% by wt., preferably 5% to 75% by wt. structuring aid and/or inert filler. Such structurants can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200-glyceryl-stearate, glucam DOE 120 (PEG Methyl Glucose Dioleate), and Hodg CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

The inert fillers which can be used in the formulations are clays such as talc, kaolin, bentonites, zeolites.

Processing
Extruded Bars:

In general, the chips defining the cleansing base are formed by mixing the ingredients of the bar phase in a mixer at a temperature of about 30° C. to 110° C. for 1 to 60 minutes, then cooling in a chill roll mill to get flakes.

The emollient rich phase is made separately by mixing the benefit components along with the base and other minor components in a mixer at a temperature of about 30° C. to 110° C. for 3 to 60 minutes, then cooling in a chill roll mill to get flakes.

The emollient rich and poor phases are separately refined and plodded in such a way that the two phases meet with each other near the cone in the final plodder. This gives well separated stripes. The billets are then cut, stamped, and packed.

In an alternative method the emollient rich components can be added in the vacuum chamber of the plodder and extruded along with the emollient poor phase to get striations.

Melt Cast Process:

In the melt cast process, the emollient rich and emollient poor phases are separately made by melting the phase components between 60–120° C. The two melts are poured in molds in such a way that the two or more phases are segregated. The phases may be in the form of stripes, swirls, one phase by the side of the other etc. The molds can be cast in pack or separate molds, which are cooled to get solid bars.

Inventive multiphase soap base cleansing bars having the compositions listed in tables 1 and 2 may be prepared. The cleansing bar of table 1 is typically prepared by an extrusion process and the cleansing bar of table 2 is typically prepared by a melt-cast process as described above. The soap base may have the fatty acid distribution and use any of the emollient, pigments, chelating agents etc. previously described. One or more phases may also be transparent, translucent, or contain particles or beads.

TABLE 1

Extrudable Formulation

| Component | Total Formula | Emollient Rich Layer | Emollient Poor Layer |
|---|---|---|---|
| Soap Base (80/20 with 12% Water) | 96.0597 | 90.459 | 98.46 |
| Tetrasodium EDTA | 0.02 | 0.02 | 0.02 |
| Tetrasodium EHDP | 0.02 | 0.02 | 0.02 |
| Titanium Dioxide | 0.50 | 0.50 | 0.50 |
| Perfume | 1.00 | 1.00 | 1.00 |
| Petrolatum | 1.20 | 4.00 | 0.0 |
| Bee Wax | 0.90 | 3.00 | 0.0 |
| Glycerin | 0.30 | 1.00 | 0.0 |
| Colorant | 0.0003 | 0.001 | 0.0 |
| | 100.00 | 100.00 | 100.00 |

TABLE 2

Melt Cast Formulation

| Component | Total Formula | Emollient Rich Layer | Emollient Poor Layer |
|---|---|---|---|
| Soap Base (60/40) | 46.4597 | 39.459 | 49.46 |
| Water | 20.0 | 20.0 | 20.0 |
| Propylene Glycol | 20.0 | 20.0 | 20.0 |
| TEA | 10.0 | 10.0 | 10.0 |
| Titanium Dioxide | 0.50 | 0.50 | 0.50 |

TABLE 2-continued

Melt Cast Formulation

| Component | Total Formula | Emollient Rich Layer | Emollient Poor Layer |
|---|---|---|---|
| Tetrasodium EDTA | 0.02 | 0.02 | 0.02 |
| Tetrasodium EHDP | 0.02 | 0.02 | 0.02 |
| DC 200 | 1.20 | 4.0 | 0.0 |
| Petrolatum | 0.90 | 3.0 | 0.0 |
| Coconut Oil | 0.90 | 3.0 | 0.0 |
| Colorant | 0.0003 | 0.001 | 0.0 |
|  | 100.0 | 100.0 | 100.0 |

The following examples are intended to further illustrate the invention and are not intended to limit the invention in any way.

Unless stated otherwise all percentages are intended to be percentages by weight.

EXAMPLE 1

A multiphase cleansing bar having the formula in table 3 was prepared. The phases were extruded as layers oriented along the major axis of the bar, and were visually distinguished by coloration in this example although coloration is optional. The emollient rich layers comprised 30% of the bar and were colored blue and the emollient poor layers comprised the remainder of the bar and were colored white.

TABLE 3

Formulation Details

| Component | Total Formula | Emollient Rich Layer | Emollient Poor Layer |
|---|---|---|---|
| Sodium cococyl isethionate | 49.422 | 42.352 | 52.452 |
| Sodium tallowate/cocoate | 6.98 | 6.7 | 7.1 |
| Water | 4.94 | 4.8 | 5.0 |
| Sodium isethionate | 4.64 | 4.5 | 4.7 |
| Coconut Fatty Acid | 3.07 | 3.0 | 3.1 |
| Sodium stearate | 2.97 | 2.9 | 3.0 |
| Cocoamidopropyl betaine | 2.77 | 2.7 | 2.8 |
| Fragrance | 1.00 | 1.000 | 1.0 |
| Sodium chloride | 0.20 | 0.200 | 0.2 |
| Titanium dioxide | 0.17 | 0.100 | 0.2 |
| Tetrasodium edta | 0.02 | 0.020 | 0.02 |
| Trisodium etidronate | 0.02 | 0.020 | 0.02 |
| BHT | 0.008 | 0.007 | 0.008 |
| Colorant | 0.0 | 0.001 | 0.0 |
| Stearic acid | 20.10 | 19.400 | 20.4 |
| Coconut Oil | 1.8 | 6.000 | 0.0 |
| Petrolatum | 1.8 | 6.000 | 0.0 |
| Tocopherol acetate | 0.09 | 0.300 | 0.0 |
| total | 100.0 | 100.0 | 100.0 |

EXAMPLE 2

A multiphase cleansing bar having the formula in table 4 was prepared. The phases were extruded as layers oriented along the major axis of the bar, and were visually distinguished by coloration in this example although coloration is optional. The emollient rich layers comprised 75% of the bar and were colored pink and the emollient poor layers comprised the remainder of the bar and were colored white.

Process Description:

White and Pink bases are made separately.

Emollient Rich Phase—The color was dissolved in perfume. The Color can also be optionally added in coconut oil and Sunflower oil. The Perfume mix and the benefit components were added in a mixer along with the rest of the ingredients and mixed. This mixed mass is passed through the refiner.

Emollient Poor Portion—The perfume is added in the rest of the base and mixed in a mixer. This mass is also passed through the refiner.

The two formulations were coextruded in such a way that the emollient rich phase gets extruded directly near the cone of the final plodding stage to get stripes. The number of stripes and the width of the stripes can be varied depending upon the requirement.

TABLE 4

Formulation Details

| Syndet Base Composition | Total Formulation | Emollient Rich Layer | Emollient Poor Layer |
|---|---|---|---|
| Sodium cococyl isethionate | 50.8 | 50.2 | 52.6 |
| Stearic acid | 19.65 | 19.4 | 20.4 |
| Sodium tallowate/cocoate | 6.8 | 6.7 | 7.1 |
| Water | 4.85 | 4.8 | 5.0 |
| Sodium isethionate | 4.55 | 4.5 | 4.7 |
| Coconut acid | 3.025 | 3.0 | 3.1 |
| Sodium stearate | 2.925 | 2.9 | 3.0 |
| Cocoamidopropyl betaine | 2.725 | 2.7 | 2.8 |
| Sunflower seed oil | 2.475 | 3.3 | 0.0 |
| Fragrance | 1.0 | 1.0 | 1.0 |
| Lanolin alcohol | 0.525 | 0.7 | 0.0 |
| Tocopherol acetate | 0.225 | 0.3 | 0.0 |
| Glycerin | 0.225 | 0.3 | 0.0 |
| Sodium chloride | 0.2 | 0.2 | 0.2 |
| Titanium dioxide | 0.125 | 0.1 | 0.2 |
| Tetrasodium edta | 0.02 | 0.02 | 0.02 |
| Trisodium etidronate | 0.02 | 0.02 | 0.02 |
| BHT | 0.007 | 0.007 | 0.008 |
| D&C red #17 | 0.0 | 0.001 | 0.0 |
| total | 100.0 | 100.0 | 100.0 |

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A multiphase cleansing bar comprising:

(a) a plurality of phases of cleansing material;

(b) each of said cleansing phases being rheologically compatible with each other;

(c) said plurality of phases having at least one emollient rich phase and emollient deficient phase, and at least one interface therebetween;

(d) said at least emollient rich phase containing an emollient composition in the amount of 0.1 to 50 weight %, said at least one emollient deficient phases uniformly containing an emollient composition in the amount of 0 to 10 weight %; and said at least one emollient rich phase having at least 2 times the emollient composition concentration compared to said at least one emollient poor phase; and wherein each of said cleansing phases have substantially the same cleansing base selected from the group consisting of a syndet base, a soap base, or mixtures thereof.

2. The cleansing bar according to claim 1, wherein said emollient rich phases have at least 2 times the emollient composition of the emollient poor phases.

3. The cleansing bar according to claim 1, wherein said emollient rich phases have at least 10 times the emollient composition of the emollient poor phases.

4. The cleansing bar according to claim 1 further comprising:
   (a) cleansing phases having substantially the same cleansing base selected from the group consisting of a syndet base, a soap base, or mixtures thereof;
   (b) said cleansing phases having alternating emollient rich phases and emollient deficient phases;
   (c) said emollient rich phases containing an emollient composition in the amount of 0.1 to 50 weight %, said emollient poor phases containing an emollient composition in the amount of 0 to 25 weight %; and said emollient rich phases having at least 2 times the emollient composition concentration compared to the emollient poor phases.

5. The cleansing bar according to claim 1, wherein the surfactant system comprises:
   (a) a first synthetic surfactant which is anionic; and
   (b) a second surfactant selected from the group consisting of a second anionic surfactant different from the first, a nonionic surfactant, an amphoteric surfactant and mixtures thereof.

6. The cleansing bar according to claim 5, wherein said the first anionic is an acyl isethionate.

7. The cleansing bar according to claim 5, wherein second surfactant is selected from the group consisting of a salt of a fatty acid, a sulfosuccinate, a betaine or a mixture thereof.

8. The cleansing bar according to claim 1, wherein the soap base comprises alkali metal salts of fatty acids derived from tallow and vegetable oil.

9. The cleansing bar according to claim 8 where the vegetable oil is selected from the group consisting of palm oil, coconut oil, palm kernel oil, palm stearin, and rice bran oil.

10. A process for making a multiphase cleansing bar according to claim 1 comprising simultaneous coextrusion of the emollient rich and emollient poor phases to get separate stripes thereof.

11. A process for making a multi-phase cleansing bar according to claim 1 comprising melt-casting of the phases to get separate stripes of emollient rich and emollient poor phases.

12. A multiphase cleansing bar comprising:
   (a) a plurality of phases of cleansing material;
   (b) each of said cleansing phases being rheologically compatible;
   (c) said plurality of phases having at least one emollient rich phase, at least one emollient deficient phase, and at least one interface therebetween;
   (d) said emollient rich phase containing an emollient composition in the amount of 0.1 to 50 weight %, said emollient deficient phase containing an emollient composition In the amount of 0 to 25 weight %; and said emollient rich phase having a higher total emollient composition concentration compared to the emollient poor phase; and wherein each of said emollient rich and poor phases have substantially the same cleansing base selected from the group consisting of a syndet base, a soap base, or a mixture thereof.

* * * * *

UNITED STATES PATENT AND TRADEMARK OFFICE
CERTIFICATE OF CORRECTION

PATENT NO. : 6,383,999 B1
DATED : May 7, 2002
INVENTOR(S) : Laurie Ann Coyle

It is certified that error appears in the above-identified patent and that said Letters Patent is hereby corrected as shown below:

<u>Title page,</u>
Item [57], ABSTRACT,
Line 12, which reads "of the skin. Chemical and Theological compatibility" should read -- of the skin. Chemical and rheological compatibility --

Signed and Sealed this

Third Day of December, 2002

JAMES E. ROGAN
*Director of the United States Patent and Trademark Office*